United States Patent [19]
Dufresne et al.

[11] Patent Number: 5,254,727
[45] Date of Patent: Oct. 19, 1993

[54] ACYCLIC TRICARBOXYLIC ACID COMPOUNDS

[75] Inventors: Claude Dufresne, East Brunswick, N.J.; E. Tracy T. Jones, Solana Beach, Calif.; Leslie A. Ferrell, Cranford, N.J.

[73] Assignee: Merck & Co., Inc., Rahway, N.J.

[21] Appl. No.: 962,547

[22] Filed: Oct. 19, 1992

[51] Int. Cl.$^5$ .............................................. C07L 59/48
[52] U.S. Cl. ..................................... 562/470; 560/60
[58] Field of Search ...................... 562/470; 560/60; 514/533, 570

[56] References Cited

U.S. PATENT DOCUMENTS 5,132,320  7/1992  Bergstrom et al. ................ 514/452

FOREIGN PATENT DOCUMENTS

405864A2  1/1991  European Pat. Off. .

OTHER PUBLICATIONS

S. Brandange et al, "Absolute Configuration and of Alkylcitric Acids" Acta Chem Scand., B31 (1977) 307-312.

S. Brandange et al, "Absolute Configuration and Enantioselective Syntheses of Spiculisporic Acid" Acta Chem. Scand. B 38 (1984) 837-844.

J. P. Lellouche et al "Syntheses of (2R, 3S); (2S, 3R) agaric acid-4-$^{14}$c, and (2R, 3R); (2S, 3S) agaric acid 4,4,5,5,-t4" Chem Abstr. 101:130185d (1984).

K. Inoue, "Hair preparations Containing 3 Hydroxy-4-dicarboxypentadecanoic Acid" Chem Abstr. 88:158285y (1978).

H. Thomas et al, "Zur Kenntniss der Agaricinsaure", Liebigs Ann. Chem., 1907, 357, 145-170.

Primary Examiner—Paul J. Killos
Attorney, Agent, or Firm—Melvin Winokur; Charles M. Caruso

[57] ABSTRACT

Two acyclic tricarboxylic acid compounds have been isolated from the fermentation of *Sporormiella intermedia*. The compounds and their derivatives may be used as antifungal agents, cholesterol lowering agents and as anticancer agents.

8 Claims, No Drawings

ACYCLIC TRICARBOXYLIC ACID COMPOUNDS

DESCRIPTION OF THE INVENTION

The present invention is directed to compounds having the structural formula

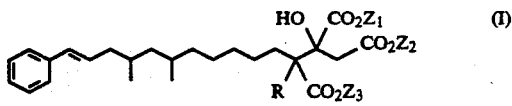

wherein
R is H or OH,
$Z_1$, $Z_2$ and $Z_3$ are each independently selected from
a) H
b) $C_1$–$C_5$ alkyl
c) $C_1$–$C_5$ alkyl substituted with a member of the group consisting of
  i) phenyl
  ii) phenyl substituted with methyl, methoxy, halogen (Cl, Br, I, F) or hydroxy; or
d) a pharmaceutically acceptable salt.

Compounds of the present invention in which $Z_1$, $Z_2$ and $Z_3$ are H, are natural products obtained by the cultivation of *Sporormiella intermedia* as hereinafter described.

When $Z_1$, $Z_2$ and $Z_3$ are H and R is H, the compound is hereinafter referred to as Compound IA and is represented by the following structure:

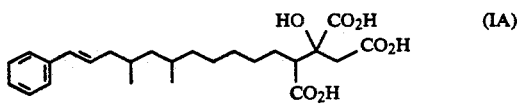

When $Z_1$, $Z_2$ and $Z_3$ are H and R is OH, the compound is hereinafter referred to as Compound IB and is represented by the following formula:

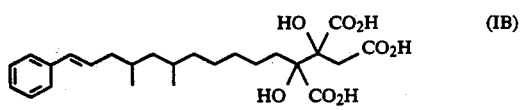

When at least one of $Z_1$, $Z_2$ and $Z_3$ is other than H, the compound may be prepared by conventional esterification procedures as hereinafter described.

The pharmaceutically acceptable salts may be prepared according to conventional procedures as hereinafter detailed. Suitable salts include sodium, potassium, ammonium, calcium, quaternary ammonium, tris-(hydroxymethyl)aminomethane, ethylenediamine, and those listed in J. Pharm. Sci. 66, 2 (1977).

The nuclear magnetic resonance (NMR) spectral data was obtained in $CD_3OD$ on a Varian XL-300 NMR spectrometer. The heteronuclear multiple coherence HMBC data was obtained on a Varian Unity 500 NMR spectrometer. The mass spectral data was obtained on a Finnegan MAT 212 mass spectrometer at 90 eV electron impact-mass spectra (EI-MS) and MAT-90 fast atom bombardment mass spectra (FAB-MS).

COMPOUND IA

NMR Spectra

The $^1H$ and $^{13}C$ NMR data for Compound IA are given below.

The characteristic $^1H$ NMR spectrum (500 MHz, $CD_3OD$) for IA is as follows: 7.33 (dd, 8.5, 1.5, 2H), 7.25 (t, 8.5, 2H), 7.15 (br tt, 8.5, 1.5), 6.36 (d, 15.5), 6.21 (dt, 15.5, 7.0), 3.07 (br d, 16.5), 2.68 (br d, 16.4), 2.63 (br d, 10.0), 2.21 (m), 2.00 (ddt, 15.0, 1.0, 7.0), 1.79 (br q, 10.0), 1.70 (oct, 7.0), 1.54 (m), 1.46 (m), 1.3–1.4 (8H), 1.07 (m), 0.97 (dt, 14.0, 7.0), 0.91 (d, 7.0, 3H), 0.88 (d, 6.5, 3H).

The characteristic $^{13}C$ NMR spectrum ($CD_3OD$) for IA is as follows: 176.67, 176.21, 173.90, 139.26, 132.44, 130.24, 129.48 (2), 127.83, 126.93 (2), 76.70, 54.82, 45.77, 42.30, 41.40, 37.85, 31.86, 31.20, 30.76, 28.85, 28.12, 27.67, 20.74, 20.63

Mass Spectrum

The molecular weight was determined to be 448 by FAB-MS and EI-MS. Silylation of the acid yielded a $448+TMS_4$ species. The trimethyl ester ($CH_2N_2$) gave a molecular ion of 490.2937 (calculated for $C_{28}H_{42}O_7$: 490.2931). Low mass ions in the EI-MS of the acid and the trimethyl ester support the structure of the phenyl-alkyl side chain.

COMPOUND IB $^1H$ NMR (500 MHz in $CD_3OD$): 7.32 (dd, 8.5, 1.5, 2H), 7.25 (t, 8.5, 2H), 7.15 (br tt, 8.5. 1.5), 6.35 (d, 15.5), 6.21 (dt, 15.5, 7.0), 3.14 (d, 17.0), 2.75 (d, 17.5), 2.30 (m), 2.21 (m), 2.10 (m), 2.00 (m, 2H), 1.69 (m), 1.55 (m), 1.3–1.4 (7H), 1.08 (m), 0.97 (m), 0.91 (d, 7.0, 3H), 0.87 (d, 6.5, 3H).

$^{13}C$ NMR ($CD_3OD$): (Partial listing) 176.6, 175.4, 173.9, 139.3, 132.4, 130.2, 129.5 (2), 127.8, 126.9 (2), 93.1, 81.6, 45.7, 41.4, 37.6, 31.6, 31.1, 20.7, 20.6.

Compounds IA and IB may be obtained by the aerobic fermentation of *Sporormiella intermedia*, ATCC 20985 or a mutant thereof. Mutant refers to an organism in which some gene on the genome is modified, leaving the gene or genes responsible for the organisms ability to produce the compounds in recoverable amounts functional and heritable.

*Sporormiella intermedia* is a coprophilous fungus isolated from cottontail rabbit dung collected in Arizona. It is disclosed in U.S. Pat. No. 5,132,320 and as stated therein, the culture has been deposited under conditions of the Budapest Treaty with the American Type Culture Collection at 12301 Parklawn Drive, Rockville, Md. 20852 and has been assigned accession number ATCC 20985.

The cultural and morphological characteristics of *Sporormiella intermedia* are as follows:

Pseudothecia maturing in 4–5 weeks on either inoculated deer dung or on oatmeal agar (Difco) at 25° C. in continuous fluorescent light. Pseudothecia on surface of inoculated deer dung single to densely gregarious, embedded, with upper 10–50% protruding above the surface, 200–300 μm in diameter, globose to subglobose, nonostiolate, glabrous, dull, uniformly black. Peridium thin, 1–2 cells thick, a textura angularis. Peridial cells isodiametric 4–8 μm in diameter, gray to dark olivaceous gray in KOH.

Asci abundant, arising from a common basal area, bitunicate, 8-spored, cylindrical, straight to slightly curved, with broad rounded apex, 120–180 μm×20–35, with a distinct basal stalk, with basal stalk 7–11 μm long. Paraphyses abundant, intermixed with asci, filamentous, septate, approximately equal in length with asci. Ascospores biseriate within the ascus, 45–53×10–12 μm, 4-celled, deeply constricted at the septa, end cells with rounded or tapered aspices, middle cells oblong to doliform, each cells with an obscure lateral germ slit, surrounded by a thin, refractive, hyaline sheath, with cells often easily separating, dark olivaceous gray in KOH.

Colonies on potato-dextrose (Difco) agar 10-12 mm in diameter in 7 days at room temperature, slightly raised, about 0.5-1 mm deep, with submerged margin, with surface felty to velutinous, cream when young, soon pale gray to dark gray, or finally dark olivaceous gray to almost black, Cartridge Buff (capitalized color names from Ridgway, R. *Color Standards and Nomenclature*, Washington, D.C. 1912), Marguerite Yellow, Olive Buff, Light Grayish Olive, Grayish Olive, Deep Grayish Olive, Iron Gray, Olivaceous Black. In reverse dull yellowish olive to olivaceous gray to dark olivaceous gray. Odors and exudates absent. Often extensive black stromatic regions develop in colonies older than 2-3 weeks. Stromatic regions may contain many embedded, confluent to gregarious pseudothecia.

Colonies 10-12 mm in diameter on potato-dextrose agar (Difco) at room temperature, felty, velutinous, smooth to slightly irregular in side view, up to 1 mm deep, with submerged margin, often sectoring into different colony colors, tough to rubbery in texture. Colony margins hyaline to pale, soon pale gray to olivaceous gray, finally dark gray to olivaceous gray, Cream Color, Pale Smoke Gray, Light Grayish Olive, Deep Olive Gray, Iron Gray, Olivaceous Black. In some sectors of old cultures, black stomatic tissues with rudimentary pseudothecia or pseudothecia-like structures are formed. Reverse pigmentation similar. Odors and exudates absent. Pigmentation and colony differentiation reduced on nutrient poor media, e.g. cornmeal agar, malt extract agar, dung extract agar, or hay extract agar.

Mycelium septate, highly branched, flexuous, often contorted to nodulose, with elements up to 8 μm in diameter, hyaline to olive or olivaceous gray in KOH. Developing a basal stromatic zone of isodiametric cells in older regions of colonies.

Pseudothecia-like structures up to 400 μm in diameter, dull, black, composed of thin-walled, isodiametric cells and filamentous hyphae, a textura angularis or a combination of textura angularis and textura intricata, with isodiametric cells up to 8 μm in diameter. Immature bitunicate asci have been observed in some of these rudimentary pseudothecia after 4-6 weeks on oatmeal agar, but cultures become moribund before asci mature.

Compounds IA and IB may be obtained by cultivating *Sporormiella intermedia*, ATCC 20985 in a nutrient medium containing sources of assimilable carbon and nitrogen and mineral salts under aerobic conditions.

The preferred sources of carbon in the nutrient medium are carbohydrates such as glucose, glycerin, starch, dextrin, and the like. Other sources which may be included are maltose, mannose, sucrose, and the like. In addition, complex nutrient sources such as oat flour, corn meal, millet, corn and the like may supply utilizable carbon. The exact quantity of the carbon source which is used in the medium will depend, in part, upon the other ingredients in the medium, but is usually found in an amount ranging between 0.5 and 5 percent by weight. These carbon sources can be used individually in a given medium or several sources in combination in the same medium.

The preferred sources of nitrogen are amino acids such as glycine, methionine, proline, threonine and the like, as well as complex sources such as yeast extracts (hydrolysates, autolysates), dried yeast, tomato paste, soybean meal, peptone, corn steep liquor, distillers solubles, malt extracts and the like. Inorganic nitrogen sources such as ammonium salts (eg. ammonium nitrate, ammonium sulfate, ammonium phosphate, etc.) can also be used. The various sources of nitrogen can be used alone or in combination in amounts ranging between 0.2 to 70 percent by weight of the medium.

The carbon and nitrogen sources are generally employed in combination, but need not be in pure form. Less pure materials which contain traces of growth factors, vitamins, and mineral nutrients may also be used. Mineral salts may also be added.

Among the nutrient inorganic salts, which can be incorporated in the culture media are the customary salts capable of yielding sodium, potassium, magnesium, calcium, phosphate, sulfate, chloride, carbonate, and like ions. Also included are trace metals such as cobalt, manganese, iron, molybdenum, zinc, cadmium, and the like.

Representative suitable solid and liquid production media may be seen in the tables which follow. Also included is a representative seed medium.

TABLE 1

|  | per liter |
|---|---|
| KF SEED MEDIUM | |
| Corn Steep Liquor | 5 g |
| Tomato Paste | 40 g |
| Oat Flour | 10 g |
| Glucose | 10 g |
| Trace Element Mix | 10 ml |
| pH = 6.8 | |
| Trace Element Mix | |
| $FeSO_4.7H_2O$ | 1 g |
| $MnSO_4.4H_2O$ | 1 g |
| $CuCl_2.2H_2O$ | 25 mg |
| $CaCl_2$ | 100 mg |
| $H_3BO_3$ | 56 mg |
| $(NH_4)_6Mo_7O_{24}.4H_2O$ | 19 mg |
| $ZnSO_4.7H_2O$ | 200 mg |

Suitable production media include those identified as F204 Medium and BRF Medium seen in Tables 2 and 3. Each medium is autoclaved (15 min. 121° C. 15 psi); 15 ml distilled water added and autoclaved (20 min. 121° C., 15 psi).

TABLE 2

|  | F204 Medium |  |
|---|---|---|
| Millet | 15.0 g/flask | |
| Base Liquid #1 | 10.0 ml/flask | |
|  | Base Liquid #1 | |
| Component |  | g/l |
| Yeast extract |  | 50.0 |
| Monosodium glutamate |  | 10.0 |
| Corn oil |  | 10.0 ml |
| Sodium tartrate |  | 10.0 ml |
| $FeSO_4.7H_2O$ |  | 1.0 |
| Distilled $H_2O$ |  | 1000.0 ml |
| no pH adjustment |  | |

TABLE 3

| BRF Medium | Brown Rice | 5.0 g/flask |
|---|---|---|
| Base Liquid #2 | 20.0 ml/flask | |
|  | Base Liquid #2 | |
| Component |  | g/l |
| Yeast extract |  | 1.0 |

TABLE 3-continued

| | |
|---|---|
| Sodium tartate | 0.5 |
| KH$_2$PO$_4$ | 0.5 |
| Distilled water | 1000.0 ml |
| no pH adjustment | |

The preferred process for production of compounds of this invention consists of inoculating spores or mycelia of *Sporormiella intermedia* into a suitable medium and then cultivating under aerobic condition.

The fermentation procedure generally is to first inoculate a preserved source of culture into a nutrient seed medium and to obtain, sometimes through a two step process, growth of the organisms which serve as seeds in the production of the active compounds. After inoculation, the flasks are incubated with agitation at temperatures ranging from 20° to 30° C., preferably 25° to 28° C. Agitation rates may range up to 400 rpm, preferably 200 to 220 rpm. Seed flasks are incubated over a period of 2 to 10 days, preferably 2 to 4 days. When growth is plentiful, usually 2 to 4 days, the culture may be used to inoculate production medium flasks. A second stage seed growth may be employed, particularly when going into larger vessels. When this is done, a portion of the culture growth is used to inoculate a second seed flask incubated under similar condition but employing shorter time.

After inoculation, the fermentation production medium is incubated for 3 to 30 days, preferably 14 to 21 days, with or without agitation (depending on whether liquid or solid fermentation media are employed). The fermentation is conducted aerobically at temperatures ranging from 20° to 40° C. If used, agitation may be at a rate of 200 to 400 rpm. To obtain optimum results, the temperatures are in the range of 22° to 28° C., most preferably 24° to 26° C. The pH of the nutrient medium suitable for producing the active compounds is in the range of 3.55 to 8.5, most preferably 5.0 to 7.5. After the appropriate period for production of the desired compound, fermentation flasks are harvested and the active compounds isolated.

The pH of the aqueous mycelial fermentation is adjusted to between 1 and 7 (preferably between 3 and 5). The aqueous mycelial fermentation is preferably mixed with a water miscible solvent such as methanol and the mycelia filtered. The active compound may then be isolated from the aqueous filtrate by several methods including:

1. Liquid-liquid extraction of the aqueous filtrate into a water immiscible solvent such as methyl ethyl ketone, ethyl acetate, diethyl ether, or dichloromethane preferably after having adjusted the pH to between 2 and 3.

2. Solid-liquid extraction of the aqueous filtrate (pH 2 to 7) onto an organic matrix such as SP207 or HP-20 and elution with an organic solvent (aqueous or nonaqueous) such as 90/10 methanol/water or 90/10 acetone/water.

3. Adsorption of the active compound from the aqueous filtrate (pH 4 to 7) onto an ionic exchange resin such as Dowex 1(Cl$^-$) and elution with a high ionic strength organic/aqueous solvent such as 90/10 methanol/aqueous 3% NH$_4$Cl. The preferred resin is AG 4-X4 (formate). The active compound can be eluted from AG 4-X4 using a low pH solution or a high salt eluant; the preferred eluant is dilute sulfuric acid in 60% acetonitrile/water. This material could then be desalted by employing either method 1 or 2 above. Each of these three methods may also be used in the further purification of the active compound.

The fraction containing active compound from the above methods could then be dried in vacuo leaving the crude active compound. The crude active compound is then generally subjected to several separation steps such as adsorption and partition chromatography, and precipitation. For each separation step, fractions are collected and combined based on results from a bioassay and/or HPLC analysis.

The chromatographic separations may be carried out by employing conventional column chromatography with ionic or nonionic adsorbent. When silica gel is the adsorbent, an alcohol/chlorohydrocarbon/organic acid mixture such as methanol/chloroform/acetic acid/water is useful as an eluant. The product may be recovered by concentrating the appropriate fractions. For reverse phase chromatography, the preferred adsorbent is a C18 or C8 bonded phase silica gel. The preferred eluant for reverse phase chromatography is a mixture of acetonitrile and water buffered at a low pH, such as with 0.1% phosphoric acid or trifluoroacetic acid. The product from reverse phase chromatography may be recovered by adding to the appropriate fractions, an equal volume of ethyl acetate and water. The organic layer is then concentrated to dryness.

The present invention is also directed to a method of inhibiting cholesterol biosynthesis which comprises administering to a subject in need of such treatment a nontoxic therapeutically effective amount of a compound represented by formula (I) and pharmaceutically acceptable salts thereof. Specifically, the compounds of this invention inhibit the enzyme squalene synthetase and are useful as antihypercholesterolemic agents for the treatment of arteriosclerosis, hyperlipidemia, familial hypercholesterolemia and the like diseases.

The intrinsic squalene synthetase inhibiting activity of representative compounds of this invention may be measured by one of the standard in vitro protocols:

A. SQUALENE SYNTHETASE ASSAY USING HEPG2 CELL ENZYME

1. Preparation of Human HepG2 Cell Enzyme

Source: HEPG2 CELL LINE (Liver, hepatoblastoma, Human) ATCC No. HB 8065

Cell Growth and Maintenance: Culture Medium: Minimum essential medium (MEM) with non-essential amino acids, sodium pyruvate, and 10% fetal bovine serum. The medium was changed twice weekly. A confluent monolayer was acheived in 1 week. The growth medium was prepared as listed below.

| Solution | Volume (ml) |
|---|---|
| 1. MEM (Gibco #320-1090AK) With Earle's salts and L-glutamine | 1000 |
| 2. Penicillin (10,000 units/mL), streptomycin (10,000 mg/mL), Gibco #600-5140 PG | 10 |
| 3. MEM sodium pyruvate, 10 mM (100X) Gibco #320-1140 | 10 |
| 4. MEM nonessential amino acids, 10 mM (100X) Gibco #320-1140AG | 10 |
| 5. L-glutamine, 200 mM (100X), Gibco #320-5030AG | 10 |
| 6. Hyclone fetal bovine serum, defined, Hyclone #A-111-L | 100 |

Subculture Procedure: The medium was removed and washed with PBS (Phosphate-Buffered Saline 15.6 mM, pH 7.0). Fresh trypsin (0.25%)-EDTA (0.02%) with Hank's Balanced Salt solution was added and the flask was allowed to stand for a minute before the trypsin solution was removed. The flask was incubated at 37° C. until cells detached. Fresh medium was added and the cells were dispersed and dispensed into new flasks. Subcultivation ratio: 1:6.

Preparation of Delipidated Serum: Fetal calf serum (100 ml) and CAB-O-Sil (2 grams) were stirred overnight at 4° C. and centrifuged at 16,000 rpm for 5 hrs. The supernantant was filtered and the serum was stored at 4° C.

48 hrs. prior to harvest, cells grown in MEM with 10% Fetal Calf serum were switched to MEM with 10% delipidated serum.

Harvest: The medium was removed and the cells were washed with PBS. Fresh trypsin (0.25%)-EDTA (0.02%) with Hank's Balanced Salt solution was added and the cells were rinsed and removed. The flask was incubated at 37° C. until the cells detached. MEM medium (6 ml/flask) was added to suspend cells and combine them into a centrifuge tube. The cells were spun at 1,000 rpm for 5 mins. The cell pellet was resuspended in PBS and recentrifuged. Cells were counted ($2.5 \times 10^9$ yield from 18 flasks (75 cm$^2$)), and resuspended in 10 mL of 50 mM HEPES (N-[2-Hydroxyethyl]piperazine-N'-[2-ethane-sulfonic acid]) containing 5 mM MgCl$_2$, 2 mM MnCl$_2$, 10 mM DTT (dithiothreitol), pH 7.5 (enzyme suspension buffer).

Cell Extracts: The cell suspension was sonicated (probe sonicator setting #60, pulse) on ice for 2 min. After a 1 min. cooling on ice, the sonication was repeated until greater than 90% of the cells were broken as observed microscopically. The cell suspension was centrifuged for 10 mins. at 10,000 rpm and the supernantant was transferred to a clean tube and centrifuged at 20,000 rpm for 20 mins. The HepG2 enzyme preparation was centrifuged at 34,000 rpm to separate the cytosol and microsomal enzymes. The resulting pellet from the 34,000 rpm centrifugation, containing the squalene synthetase, was resuspended in 5 mL of enzyme suspension buffer. The enzyme suspension was diluted 1 to 1,536 and used to perform the squalene synthetase assay using 3 μM $^3$H-farnesyl pyrophosphate as the substrate.

2. The Assay

Reactions were performed in 1.2 mL polypropylene tube strips of 8. Buffer mixture and substrate mixture for the assay were prepared from the following solution:

Buffer mixture contains 270 mM HEPES, pH 7.5, 20 mM potassium fluoride and 5.4 mM dithiothreitol (DTT). 55 μL of this mixture was used per assay. The final concentrations of HEPES, KF and DTT in the assay are 150 mM, 11 mM and 3 mM respectively.

Substrate mixture:

| Stock concentration | μL used per assay | Final concentration |
|---|---|---|
| 1. MgCl$_2$, 55 mM | 10 | 5.5 mM |
| 2. NADPH*, 10 mM (made fresh) | 10 | 1 mM |
| 3. Squalene Expoxidase inhibitor, Banyu FW-439H, 0.5 mg per mL | 0.02 | 0.1 μg per mL |
| 4. $^3$H-farnesyl-pyrophosphate, 25 μM, 20 Ci per mole | | |
| 5. Farnesyl-pyrophosphate, 3 mM | 0.098 | 2.94 μM |
| 6. Water | 9.63 | |

*β-nicotinamide adenine dinucleotide phosphate, reduced form

For each reaction, 55 μL of buffer mixture was taken with 5 μL of an inhibitor solution in MeOH and 10 μL of diluted enzyme (1 to 1536 as described in the enzyme preparation, the final protein concentration of enzyme in the assay is 1.2 μg per mL). The reaction was initiated by the addition of 30 μL of substrate solution and the mixture was incubated at 30° C. for 20 minutes. The reactions were stopped by the addition of 100 μL of 95% EtOH, vortexed, and 100 μL of a suspension of 1 gram per mL of Bio-Rad AG 1×8 resin (400 mesh, chloride form) was then added, vortexed. 800 μL of heptane was added to each tube strip and the strips were capped and vortexed for 10 minutes. 400 μL of heptane layer was then removed into a minivial and mixed with 2.5 mL of scintillation fluid and the radioactivity was determined by liquid scintillation counting. The controls were run with 5 μL of MeOH and blanks were run with the addition of 100 μL of 95% EtOH to denature the enzyme before the addition of the substrate mixture to the assay tube.

Percent inhibition is calculated by the formula:

$$\frac{(Control - Sample) \times 100}{Control - Blank}$$

IC$_{50}$ values were determined by plotting the log of the concentration of the test compound versus the percentage inhibition. The IC$_{50}$ is the concentration of inhibitor that gives 50% inhibition as determined from these plots.

In a representative demonstration of inhibition of squalene synthetase from human HEPG2 cells, Compound IA exhibited an IC$_{50}$ value of about 145 nM.

B. SQUALENE SYNTHETASE ASSAY USING RAT LIVER ENZYME

1. Preparation of Enzyme

Preparation of Rat Liver Microsomes: Male, Charles River CD rats (120 to 150 g) were fed a diet containing 0.1% lovastatin for 4 days. The livers from these rats were homogenized in 5 volumes (ml/g) of ice cold 50 mM HEPES (4-(2-hydroxyethyl)-1-piperazine-ethane-sulfonic acid), 5 mM EDTA(ethylenediaminetetra-acetic acid) pH 7.5 with a Potter-Elvehjem type tissue grinder. The homogenate was centrifuged twice at 20,000×g for 15 minutes at 4° C., discarding the pellet each time. The supernatant was then centrifuged at 100,000×g for 1 hour at 4° C. The resulting microsomal pellet was resuspended in a volume of the above homogenizing buffer equal to one-fifth the volume of the original homogenate. This microsomal preparation has a protein concentration of about 7 mg/ml. The microsomal suspensions were stored in aliquots at −70° C. Squalene synthetase activity in these aliquots is stable for at least several months.

Partial Purification of Prenyl Transferase: Prenyl transferase was purified to use in the enzymatic synthesis of radiolabelled farnesyl pyrophosphate [FPP]. Prenyl transferase was assayed by the method of Rilling (Methods in Enzymology 110, 125-129 (1985)) and a unit of activity is defined as the amount of enzyme that will produce 1 μmole of farnesyl pyrophosphate per minute at 30° C. in the standard assay.

The livers of 23 forty-day old male rats that had been fed 5% cholestyramine plus 0.1% lovastatin were homogenized in a Waring blender in 1 liter of 10 mM mercaptoethanol, 2 mM EDTA, 25 μM leupeptin, 0.005% phenylmethyl sulfonyl fluoride pH 7.0 containing 0.1 trypsin inhibitor units of aprotinin/ml. The homogenate was centrifuged at 20,000×g for 20 minutes. The supernatant was adjusted to pH 5.5, with 6N HOAc and centrifuged at 100,000×g for 1 hour. This supernatant was adjusted to pH 7.0 with 3N KOH and a 35-60% ammonium sulfate fraction taken. The 60% pellet was redissolved in 60 ml of 10 mM potassium phosphate, 10 mM mercaptoethanol, 1 mM EDTA pH 7.0 (Buffer A) and dialyzed against two 1 liter changes of Buffer A. This dialyzed fraction was applied to a 12.5×5 cm column of DEAE-sepharose (diethylaminoethyl sepharose) 4 B equilibrated with Buffer A. The column was washed with 700 ml of Buffer A and a 1 liter gradient from Buffer A to 100 mM potassium phosphate, 10 mM mercaptoethanol, 1 mM EDTA pH 7.0. Fractions having a specific activity greater than 0.20 units/mg were combined, solid ammonium sulfate was added to bring to 60% saturation and pelleted. The pellet was dissolved in 8 ml of 10 mM Tris, 10 mM β-mercaptoethanol pH 7.0 (Buffer B). The redissolved pellet was taken to 60% saturation with ammonium sulfate by adding 1.5 volumes of saturated ammonium sulfate in Buffer B. This ammonium sulfate suspension contained 3.5 units/ml with a specific activity of 0.23 units/mg and was free of isopentenyl pyrophosphate isomerase activity. This ammonium sulfate suspension was used for the synthesis of [4-$^{14}$C]farnesyl-pyrophosphate and its activity was stable stored at 4° C. for at least 6 months.

Enzymatic Synthesis of [4-$^{14}$C]farnesylpyrophosphate: The solvent (ethanol: 0.15N NH$_4$OH, 1:1) was removed from 55 μCi of [4-$^{14}$C]isopentenyl pyrophosphate (47.9 μCi/μmole) by rotary evaporation. Six hundred microliters of 100 mM Tris, 10 mM MgCl$_2$, 4 mM dithiothreitol pH 7.5 was added and the solution was transferred to a 1.5 ml Eppendorf centrifuge tube. Geranyl-pyrophosphate, 250 μl of a 20 mM solution, and 50 μl of the ammonium sulfate suspension of prenyl transferase were added to initiate the reaction. This incubation contained 5 μmoles of geranyl pyrophosphate, 1.15 μmoles of isopentenyl pyrophosphate, 6 μmoles of MgCl$_2$ and 0.18 units of prenyl transferase in a volume of 900 μl. The incubation was conducted at 37° C. During the incubation, the mix turned cloudy white as the newly formed magnesium complex of farnesyl pyrophoshate precipitated out of solution. The [4-$^{14}$C]farnesyl pyrophosphate was collected by centrifugation for 3 minutes at 14,000 rpm in an Eppendorf centrifuge tube, the supernatant removed, and the pellet was dissolved in 1.0 ml of 50 mM HEPES, 5 mM EDTA, pH 7.5 . The yield was 50.7 μCi (92%) of [4-$^{14}$C]farnesyl pyrophosphate. The [4-$^{14}$C]farnesyl pyrophosphate was stored in aliquots at −70° C.

2. The Assay

Reaction were performed in 16×125 mm screw cap test tubes. A batch assay mix was prepared from the following solution:

|   | μl per assay | volume for 50 assays |
|---|---|---|
| 1. 250 mM HEPES pH 7.5 | 20 | 1000 |
| 2. NaF 110 mM | 10 | 500 |
| 3. MgCl$_2$ 55 mM | 10 | 500 |
| 4. Dithiothreitol 30 mM | 10 | 500 |
| 5. NADPH 10 mM (made fresh) | 10 | 500 |
| 6. [4-$^{14}$C]farnesyl-pyrophosphate 47.9 μCi/μmole, and 0.025 μCi/3.0 μl | 3.0 | 150 |
| 7. H$_2$O | 24 | 1200 |

This assay mix was degassed under a vacuum and flushed with N$_2$. Solutions of the squalene synthetase inhibitors were prepared either in DMSO or MeOH and a 1:120 dilution of the microsomal protein was made with the original homogenizing buffer. For each reaction, 87 μl of the assay mix was taken with 3 μl of an inhibitor solution (DMSO or MeOH in the controls), warmed to 30° C. in a water bath and then the reaction was initiated by the addition of 10 μl of the 1:120 dilution of microsomal protein (0.6 μg protein total in the assay). The reactions were stopped after 20 minutes by the addition of 100 μl of a 1:1 mix of 40% KOH with 95% EtOH. The stopped mix was heated at 65° C. for 30 minutes, cooled, 10 ml of heptane was added and the mix was vortexed. Two grams of activated alumina was then added, the mix vortexed again, the alumina allowed to settle and 5 ml of the heptane layer was removed. Ten ml of scintillation fluid was added to the heptane solution and radioactivity was determined by liquid scintillation counting.

Percent inhibition is calculated by the formula:

$$1 - \frac{[\text{Sample} - \text{Blank}]}{[\text{Control} - \text{Blank}]} \times 100$$

IC$_{50}$ values were determined by plotting the log of the concentration of the test compound versus the percentage inhibition. The IC$_{50}$ is the concentration of inhibitor that give 50% inhibition as determined from these plots.

In a representative determination, Compound IA exhibited a IC$_{50}$ value of 767 nM.

For treating diseases such as those previously indicated compositions containing a squalene synthetase inhibiting amount of Compound I is administered to a patient in need of therapy. The therapeutic amount may be administered orally or parenterally, but it is usually desirable to use the oral route. Doses are dependent on the condition of the patient, such as age, severity, body weight, and the like, but a daily dose of between 20 to 2000 mg, preferably about 20 to 100 mg, may be administered, generally in multiple doses. Higher doses may be employed if required.

The compounds may be administered in the salt form. The pharmaceutically acceptable salts of the compounds include those formed from sodium, potassium, aluminum, calcium, lithium, magnesium, zinc, and from bases such as ammonia, ethylenediamine, N-methylglucamine, lysine, arginine, ornithine, choline, N-N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. This invention includes salts of one, two or three of the carboxyl groups of formula (I).

The compounds of this invention may also be administered in combination with other cholesterol lowering agents such as those which inhibit an enzymatic pathway in the biosynthesis of cholesterol. Example of such agents would include but are not limited to HMG-CoA reductase inhibitors, HMG-CoA synthase inhibitors, and squalene expoxidase inhibitors. Illustrative of such inhibitors are lovastatin, simvastatin, pravastatin and fluvastatin. Other cholesterol lowering agents that may be administered include niacin, probucol, and the fibric acids, clofibrate and gemfibrozil. Appropriate daily dosages for adults are niacin (2–8 gm), probucol (up to 100 mg) clofibrate (up to 2 gm) and gemfibrozil (800–1500 mg).

The compounds of this invention may also be coadministered with pharmaceutically acceptable nontoxic cationic polymers capable of binding bile acids in a non-reabsorbable form in the gastrointestinal tract. Examples of such polymers include cholestyramine, colestipol and poly[methyl-(3-tri-methylaminopropyl)imino-trimethylene dihalide]. The relative amounts of the compounds of this invention and these polymers is between 1:100 and 1:15,000.

The present compounds also demonstrate broad spectrum antifungal activity as determined by broth dilution methods. The compounds are active towards both filamentous fungi and yeasts. The sensitivity of filamentous fungi and yeast was determined using inhibitor dilution assays in microtiter format. The compounds were dissolved in DMSO at 5 mg/mL and serially diluted by two-fold dilutions in 50 µL of sterile water. Exponential phase Candida, Cryptococcus, Ustilago and Saccharomyces cells were diluted in fresh liquid synthetic medium (Difco Yeast Nitrogen Base supplemented with 2% glucose (SM)) such that the inoculum was $1 \times 10^4$ cells/mL. Aspergillus spores were harvested from a well-sporulated Sabouraud Dextrose Agar slant in 0.4% Tween 80 and diluted into media to give an inoculum of $1 \times 10^3$ spores/mL. The wells were filled with 150 µl of inoculated media. The final drug concentration tested ranged from 50 to 0.078 µg/mL. The microtiter dishes were incubated at 29° C. for 20 to 48 hours. The minimum inhibitory concentration (MIC) is defined as the lowest concentration to prevent visible growth after incubation for 20 hours at 29° C. for the yeasts and 24 to 48 hours at 29° C. for the filamentous fungi. Representative of the antifungal activity are the minimum inhibitory concentration data shown below.

| Organism | Minimum Inhibitory Concentration (MIC) µg/mL |
|---|---|
| Cryptococcus neoformans MY 2061 | 12.5 |
| Candida albicans MY 1055 | >50. |
| Aspergillus fumigatus MF 4839 | 25.0 |
| Ustilago zeae MF 1996 | 3.15 |
| Saccharomyces cerevisiae W30[3] | 50 |

In view of the foregoing, the present invention is also directed to a method of treating fungal infections which comprises administering to a subject in need of treatment, a nontoxic antifungally effective amount of a compound represented by the structural formula (I), particularly IA and IB and the pharmaceutically acceptable salts thereof.

The compounds of this invention are adaptable to being utilized in various applications of antifungal compositions. In such use, compounds may be admixed with a biologically inert carrier, generally with the aid of a surface active dispersing agent, the nature of which would vary depending on whether the use is for the control of pathogens infecting mammals such as man, or birds or reptiles, or for control of fungi in agriculture such as in soil or plant parts, or for the control of fungi in inanimate objects.

In compositions for medical applications, the compounds may be admixed with a pharmaceutically acceptable carrier, the nature of which will vary depending on whether the composition is to be topical, parenteral or oral.

If said application is to be topical, the drug may be formulated in conventional creams and ointments such as white petroleum, anhydrous lanolin, cetyl alcohol, cold cream, glyceryl monostearate, rose water and the like.

For parenteral applications, the compounds may be formulated in conventional parenteral solutions such as 0.85 percent sodium chloride or 5 percent dextrose in water, or other pharmaceutically acceptable compositions.

Compositions for oral administration may be prepared by intimately mixing the component drugs with any of the usual pharmaceutical media, including, for liquid preparations, liquid carriers such as water, glycols, oils, alcohols, and the like; and for solid preparations such as capsules and tablets, solid carriers such as starches, sugars, kaolin, ethyl cellulose, surface active dispersing agents, generally with lubricant such as calcium stearate, together with binders, disintegrating agents and the like.

These compositions are then administered in amounts sufficient to obtain the desired antifungal effect. For medical application, the method comprises administering to a subject in need of treatment a therapeutically effective antifungal amount of a compound of Formula I. The appropriate doses will vary depending on age, severity, body weight and other conditions. For topical application the compositions are applied directly to the area where control is desired. For internal administration, the composition may be applied by injection or may be administered orally.

For non-medical application, the product of the present invention, either singly or as a mixture, may be employed in compositions in an inert-carrier which includes finely divided dry or liquid diluents, extenders, fillers, conditioners and excipients, including various clays, diatomaceous earth, talc, and the like, or water and various organic liquids such a lower alkanols, for example ethanol and isopropanol, or kerosene, benzene, toluene and other petroleum distillate fractions or mixtures thereof.

These compositions may be employed by applying to the surface of or incorporating in the medium to be protected. For the control of rice blast, tomato late blight, tomato early blight, wheat leaf rust, bean powdery mildew and tomato Fusarium wilt, the compositions may be applied directly to the plant in topical application or administered to the soil for systemic application. The method comprises administering to the affected plant, soil or medium to be protected an antifungally effective amount of the compound of Formula I.

Furthermore, the compounds of the present invention may inhibit farnesyl-protein transferase and thereby inhibit farnesylation of the RAS protein which would block the ability of RAS to transform normal cells to cancer cells.

The intrinsic farnesyl-protein transferase (FTase) activity of representative compounds of this invention is measured by the assays described below:

RASIT ASSAY I

Farnesyl-protein transferase (FTase) from bovine brain is chromatographed on DEAE-Sephacel (Pharmacia, 0–0.8M NaCl gradient elution), N-octyl agarose (Sigma, 0–0.6M NaCl gradient elution), and a mono Q HPLC column (Pharmacia, 0–0.3M NaCl gradient). Ras-CVLS at 3.5 $\mu$M, 0.25 $\mu$M [$^3$H]FPP, and the indicated compounds are incubated with this partially purified enzyme preparation.

RASIT ASSAY II

Farnesyl-protein transferase (FTase) from bovine brain is chromatographed on DEAE-Sephacel (Pharmacia, 0–0.8M NaCl gradient elution), N-octyl agarose (Sigma, 0–0.6M NaCl gradient elution), and a mono Q HPLC column (Pharmacia, 0–0.3M NaCl gradient). Ras-CVLS at 1.0 $\mu$M, 0.5 $\mu$M [$^3$H]FPP, and the indicated compounds are incubated with this partially purified enzyme preparation. The Ftase data is a measure of the ability of the test compound to inhibit Ras farnesylation in vitro.

The pharmaceutical compositions containing the compounds of structural formula (I) inhibit farnesyl-protein transferase and the farnesylation of the oncogene protein Ras. These compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, and myeloid leukemias.

The present invention also encompasses a method of the treatment of cancer, comprising the administration of a pharmaceutical composition comprising a therapeutically effective amount of the compounds of this invention, with or without pharmaceutically acceptable carriers or diluents.

Suitable compositions of this invention include aqueous solutions comprising compounds of this invention and pharmacologically acceptable carrier, e.g. saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In an exemplary application, the compound may be administered to a human patient in an amount between about 0.1 mg/kg of body weight to about 20 mg/kg of body weight of a mammal per day, preferably of between 0.5 mg/kg of body weight to about 10 mg/kg of body weight of a mammal a day.

The compositions for any of the foregoing uses contain at least a therapeutic amount of the active compound. Generally, compositions contain at least 1 percent by weight of Compound I. Concentrate compositions may contain 90 percent or more by weight.

These compositions also may be presented in unit dosage form in ampoules or in multidose containers, preferably with added preservative. Alternatively, the active ingredients may be in powder form for reconstituting with a suitable vehicle prior to administration.

The term "unit dosage form" as used in the specification and claims refer to physically discrete units, each unit containing a predetermined quantity of active ingredient calculated to produce the desired therapeutic effect in association with the pharmaceutical carrier. Examples of such unit dosage forms are tablets, capsules, pills, powder packets, wafers, measured units in ampoules or in multidose containers and the like. A unit dosage of the present invention may contain from 10 $\mu$g to 1000 milligrams of one of the compounds.

The following examples illustrate the invention but are not be to construed as limiting.

EXAMPLE I

A. Fermentation 250 milliliter flasks containing 54 milliliters of KF medium were inoculated from frozen vials of *Sporormiella intermedia* ATCC 20985 incubated at 25° C. for four days at 220 rpm. A 20 ml sample was used to inoculate each of four 2 L flasks containing 500 ml of KF medium, which were incubated at 25° C. for two days at 220 rpm. The contents of the four flasks were pooled for use as inoculum for a 300 L seed fermentor containing 180 L of KF medium and 2 ml/L polypropylene glycol P-2000 (to reduce foaming). The seed fermentor was operated for two days at a temperature of 25° C., an air flow of 180 L/min, a pressure of 0.7 kg/cm$^2$, and an agitator speed of 150 rpm.

Five 500 L production fermentors were used, each containing 400 L of CPP medium (cerelose, Pharmamedia (cottonseed flour), phosphate) of the following composition per liter: glucose monohydrate, 50 g; Pharmamedia (cottonseed flour), 20 g; KH$_2$PO$_4$, 9 g; P-2000, 4 ml. The production fermentors were each inoculated with 50 L of broth from the seed fermentor, and initially operated at a temperature of 23.5° C., an air flow of 300 L/min, a pressure of 0.7 kg/cm$^2$, and an agitator speed of 80 rpm. The air flow rate and the agitator speed were increased during the fermentation to maintain a minimum dissolved oxygen concentration of 25% of atmospheric saturation. The five batches were harvested after 187 hours, and combined.

B. Isolation

Approximately 2000 liters of the broth from the above-described fermentation was centrifuged to separate the mycelium. The wet mycelium was extracted twice with methanol to obtain 3000 liters of methanol extract which was then adsorbed in two 1500 liter portions onto two columns of DOWEX-1 (Dow Chemical Company) (Cl cycle; 56 L resin bed volume each). After adsorption, the columns were washed with 110 liters of 80% methanol/water and then with 110 liters of 90% methanol/water. The columns were then eluted with 3% ammonium chloride in 90% methanol/water collecting 56 liter fractions. Fractions 3–6 from both columns were combined to form a rich cut which was diluted with 225 liters of water to obtain a final volume of 680 liters. The solution was then loaded onto an HP-20 column (56 liter resin bed volume) and the column eluted consecutively with 56 liters of each of 50% methanol/water, 60% methanol/water, 70% methanol/water, 80% methanol/water and 90% methanol/water. The column was then eluted further with an additional 19 liters of 90% methanol/water to form Eluate A.

A 4-liter aliquot of Eluate A, obtained by elution with 90% methanol/water, was concentrated to about 500 milliliters. The aqueous concentrate was acidified to pH 2.5 with 2N HCl and then 500 milliliters of ethyl acetate was added and the mixture stirred. The ethyl acetate layer was then separated and concentrated to dryness. The residue was dissolved in 1 milliliter of methanol and injected on a preparative reverse phase HPLC column (DYNAMAX) C8, 8 $\mu$m, 21.4 mm ID×250 mm+guard column) eluting with 70% acetonitrile/30% dil. aqueous phosphoric acid (0.1%) with a flow rate of 10 ml/min. Fractions were collected at 0.5 minute intervals. Fractions 33 to 38 were combined and equal volumes of water and ethyl acetate were added. The ethyl acetate layer was separated and concentrated to dryness. The residue was dissolved in 100 microliters of methanol and injected onto a semi-preparative reverse phase HPLC column (DYNAMAX C8, 8 $\mu$m, 10.0 mm ID×250 mm+guard column) eluting with 65% acetonitrile/35% dilute aqueous phosphoric acid (0.1%) with a flow rate of 4 ml/min. Fractions were collected at 0.5 minute intervals.

Fraction 28 was diluted with 2 milliliters of water and 2 milliliters of ethyl acetate. The ethyl acetate layer was separated and concentrated to dryness to obtain 0.9 mg of Compound IA.

Fractions 29-30 were combined and diluted with 4 milliliters of water and 4 milliliters of ethyl acetate. The ethyl acetate layer was separated and concentrated to dryness to obtain 1.3 milligrams of Compound IB.

EXAMPLE II

Gelatin capsules suitable for oral administration are prepared by mixing for each capsule amount 20 milligrams of the Compound IA with sufficient finely divided lactose to provide an amount of 580 to 590 milligrams to fill a size 0 capsule.

EXAMPLE III

Capsules containing Compound IB are prepared in a similar manner by substituting Compound IB for Compound IA.

EXAMPLE IV

Preparation of an Ammonium Salt

A 0.1 mmol sample of the free acid of Compound (IB) is dissolved in 10 ml of ethyl acetate. The resulting solution is saturated with gaseous ammonia, upon which the ammonium salt precipitates from solution.

EXAMPLE V

A solution of 0.1 mmol of Compound IA in 10 ml of methanol is treated with an aqueous or methanolic solution containing 0.3 mmol of potassium hydroxide and the solvent then evaporated to obtain the tri-potassium salt. Addition of between 0.1 and 0.3 mmol of potassium hydroxide yields analogously mixtures of the mono-potassium, di-potassium and tri-potassium salts whose composition depends upon the exact amount of potassium hydroxide added.

In a similar fashion, the sodium and lithium salts of Compound IA and IB can be prepared.

EXAMPLE VI

Preparation of a Calcium Salt

A solution of 0.1 mmol of Compound IA in 20 ml of 6:4 methanol/water is treated with an aqueous solution of 0.1 mmol of calcium hydroxide. The solvents are evaporated to obtain the corresponding calcium salts.

EXAMPLE VII

Preparation of an Ethylenediamine Salt

A solution of 0.1 mmol of Compound IB in 10 ml of methanol is treated with 0.1 mmol of ethylenediamine. Evaporation of the solvent affords the ethylenediamine salt.

The procedure can also be applied to the preparation of the N,N"-dibenzylethylenediamine salt.

EXAMPLE VIII

Preparation of a Tris(hydroxymethyl)aminomethane salt

To a solution of 0.1 mmol of Compound IB in 10 ml of methanol is added from 0.1 to 0.3 mmol of tris(hydroxymethyl)aminomethane dissolved in 10 ml of methanol. Evaporation of the solvent gives a corresponding salt form of Compound (I), the exact composition of which is determined by the molar ratio of amine added.

The method can also be applied to other amines such as, but not limited to: diethanolamine and diethylamine.

EXAMPLE IX

The preparation of a L-arginine salt

To a solution of 0.1 mmol of the Compound IA in 10 ml of 6:4 methanol/water is added an aqueous solution of 0.1–0.3 mmol of L-arginine. Evaporation of the solvent provides the title salt, the exact composition of which is determined by the molar ratio of amino acid to the free acid of Compound (I).

Similarly prepared are the salts of L-ornithine, L-lysine, and N-methylglucamine.

EXAMPLE X

Preparation of a Trimethyl Ester of Compound IA

A solution of 2 mg of Compound IA in 0.5 ml of acetonitrile is mixed at room temperature with 10 equivalents of 1,8-diazobicyclo[5.4.0]undec-7-ene (DBU) and 10 equivalents of methyl iodide. After 2 hours the reaction is diluted with 10 ml of dichloromethane and washed successively with 10 ml of 0.1M phosphoric acid, 10 ml of water, 10 ml of saturated sodium bicarbonate and 10 ml of water. After drying over sodium sulfate, the organic layer is concentrated and the residue is chromatographed on silica gel using mixtures of hexane and ethyl acetate to yield a trimethyl ester of IA.

The method of Example X is also suitable for the preparation of other ester derivatives such as 1)ethyl and another lower alkyl esters and 2)benzyl and hydro, halogen, methoxy or methyl substituted benzyl esters.

What is claimed is:

1. A compound having the formula

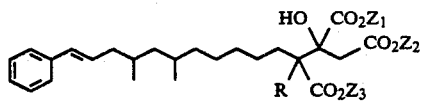  (I)

wherein
R is H or OH,
$Z_1$, $Z_2$ and $Z_3$ are each independently selected from
a) H
b) $C_1$-$C_5$ alkyl
c) $C_1$-$C_5$ alkyl substituted with a member of the group consisting of
   i) phenyl
   ii) phenyl substituted with methyl, methoxy, halogen (Cl, Br, I, F) or hydroxy; or
a pharmaceutically acceptable salt thereof.

2. A compound of claim 1 which is

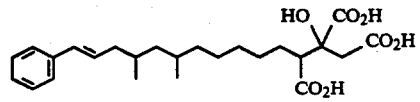

or a pharmaceutically acceptable salt thereof.

3. A compound of claim 1 which is

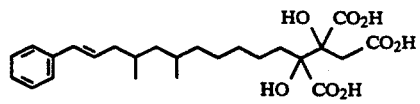

or a pharmaceutically acceptable salt thereof.

4. A pharmaceutical composition comprising a non-toxic therapeutically effective amount of a compound of claim 1 and a pharmaceutically acceptable carrier.

5. A composition according to claim 4 in unit dose form wherein the compound of claim 1 is present in an amount of from 10 μg to 1000 mg.

6. A method of inhibiting squalene synthetase comprising administering to a subject in need of such treatment a non-toxic therapeutically effective amount of a compound of claim 1.

7. A method of inhibiting fungal growth comprising applying to the area where growth is to be controlled, an antifungally effective amount of a compound of claim 1.

8. A method of inhibiting farnesyl-protein transferase and farnesylation of the oncogene protein Ras, comprising administering to a subject in need of such treatment, a therapeutically effective amount of the compound of claim 1.

* * * * *